US006482595B2

(12) United States Patent
Shuber et al.

(10) Patent No.: US 6,482,595 B2
(45) Date of Patent: *Nov. 19, 2002

(54) METHODS FOR DETECTING MUTATIONS USING PRIMER EXTENSION

(75) Inventors: Anthony P. Shuber, Milford, MA (US); William Pierceall, Wellesley, MA (US)

(73) Assignee: Exact Sciences Corporation, Maynard, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/940,225

(22) Filed: Aug. 27, 2001

(65) Prior Publication Data

US 2002/0045183 A1 Apr. 18, 2002

Related U.S. Application Data

(63) Continuation of application No. 09/371,991, filed on Aug. 11, 1999, now Pat. No. 6,280,947.

(51) Int. Cl.[7] .............................. C12Q 1/68; C12P 19/34
(52) U.S. Cl. ........................................................... 435/6
(58) Field of Search ..................................... 435/6, 91.2

(56) References Cited

U.S. PATENT DOCUMENTS

| | | | |
|---|---|---|---|
| 4,101,279 A | 7/1978 | Aslam ........................... 23/259 |
| 4,309,782 A | 1/1982 | Paulin ............................ 4/661 |
| 4,333,734 A | 6/1982 | Fleisher ....................... 23/230 |
| 4,445,235 A | 5/1984 | Slover et al. ................ 4/144.2 |
| 4,535,058 A | 8/1985 | Weinberg et al. ............... 435/6 |
| 4,683,195 A | 7/1987 | Mullis et al. ................... 435/6 |
| 4,705,050 A | 11/1987 | Markham ................... 128/749 |
| 4,735,905 A | 4/1988 | Parker ......................... 436/174 |
| 4,786,718 A | 11/1988 | Weinberg et al. ........... 530/387 |
| 4,857,300 A | 8/1989 | Maksem ........................ 424/3 |
| 4,871,838 A | 10/1989 | Bos et al. ...................... 536/27 |
| 4,981,783 A | 1/1991 | Augenlicht .................... 435/6 |
| 4,982,615 A | 1/1991 | Sultan et al. ............ 73/864.51 |
| 5,075,217 A | 12/1991 | Weber ............................ 435/6 |
| 5,087,617 A | 2/1992 | Smith ........................... 514/44 |
| 5,126,239 A | 6/1992 | Livak et al. .................... 435/6 |
| 5,137,806 A | 8/1992 | LeMaistre et al. .............. 435/6 |
| 5,149,506 A | 9/1992 | Skiba et al. ................. 422/102 |
| 5,196,167 A | 3/1993 | Guadagno et al. ............ 422/56 |
| 5,202,231 A | 4/1993 | Drmanac et al. ............... 435/6 |
| 5,248,671 A | 9/1993 | Smith ........................... 514/44 |
| 5,272,057 A | 12/1993 | Smulson et al. ................ 435/6 |
| 5,302,509 A | 4/1994 | Cheeseman .................... 435/6 |
| 5,330,892 A | 7/1994 | Vogelstein et al. ............. 435/6 |
| 5,331,973 A | 7/1994 | Fiedler et al. ............... 128/760 |
| 5,348,855 A | 9/1994 | Dattagupta et al. ............ 435/6 |
| 5,352,775 A | 10/1994 | Albertsen et al. .......... 536/23.1 |
| 5,362,623 A | 11/1994 | Vogelstein et al. ............. 435/6 |
| 5,369,004 A | 11/1994 | Polymeropoulos et al. .... 435/6 |
| 5,378,602 A | 1/1995 | Polymeropoulos et al. .... 435/6 |
| 5,380,645 A | 1/1995 | Vogelstein ..................... 435/6 |
| 5,380,647 A | 1/1995 | Bahar ........................ 435/7.23 |
| 5,382,510 A | 1/1995 | Levine et al. ................... 435/6 |
| 5,409,586 A | 4/1995 | Kamahori et al. ....... 204/182.8 |
| 5,458,761 A | 10/1995 | Kamahori et al. .......... 204/299 |
| 5,463,782 A | 11/1995 | Carlson et al. ................ 4/661 |
| 5,466,576 A | 11/1995 | Schulz et al. .................. 435/6 |
| 5,468,610 A | 11/1995 | Polymeropoulos et al. .... 435/6 |
| 5,468,613 A | 11/1995 | Erlich et al. ................... 435/6 |
| 5,489,508 A | 2/1996 | West et al. ..................... 435/6 |
| 5,492,808 A | 2/1996 | de la Chapelle et al. ....... 435/6 |
| 5,496,470 A | 3/1996 | Lenhart ....................... 210/222 |
| 5,508,164 A | 4/1996 | Kausch et al. .................. 435/6 |
| 5,512,441 A | 4/1996 | Ronal ............................ 435/6 |
| 5,514,547 A | 5/1996 | Balazs et al. ................... 435/6 |
| 5,527,676 A | 6/1996 | Vogelstein et al. ............. 435/6 |
| 5,532,108 A | 7/1996 | Vogelstein ................ 435/240.2 |
| 5,545,527 A | 8/1996 | Stevens et al. ................. 435/6 |
| 5,552,283 A | 9/1996 | Diamandis et al. ............ 435/6 |
| 5,569,584 A | 10/1996 | Augenlicht .................... 435/6 |
| 5,571,676 A | 11/1996 | Shuber .......................... 435/6 |
| 5,578,458 A | 11/1996 | Caskey et al. ................. 435/6 |
| 5,580,729 A | 12/1996 | Vogelstein ..................... 435/6 |
| 5,589,335 A | 12/1996 | Kearney et al. ................ 435/6 |
| 5,610,287 A | 3/1997 | Nikiforov et al. ......... 536/24.3 |
| 5,616,463 A | 4/1997 | Fornace, Jr. et al. ........... 435/6 |
| 5,627,032 A | 5/1997 | Ulanovsky ..................... 435/6 |
| 5,635,347 A | 6/1997 | Link et al. ..................... 435/6 |
| 5,650,277 A | 7/1997 | Navot et al. ................... 435/6 |
| 5,670,325 A | 9/1997 | Lapidus et al. ................. 435/6 |
| 5,709,998 A | 1/1998 | Kinzler et al. ................. 435/6 |
| 5,741,650 A | 4/1998 | Lapidus et al. ................. 435/6 |
| 5,759,777 A | 6/1998 | Kearney et al. ................ 435/6 |
| 5,830,665 A | 11/1998 | Shuber et al. .................. 435/6 |
| 5,834,193 A | 11/1998 | Kozlowski et al. ............ 8/408 |
| 5,846,710 A | 12/1998 | Bajaj ............................. 435/6 |
| 5,885,775 A | 3/1999 | Haff et al. ..................... 435/6 |
| 5,888,778 A | 3/1999 | Shuber ...................... 435/91.1 |
| 5,888,819 A | 3/1999 | Goelet et al. .................. 435/5 |
| 5,928,870 A | 7/1999 | Lapidus et al. ................. 435/6 |
| 6,013,431 A | 1/2000 | Soderlund et al. ............. 435/5 |
| 6,153,379 A | 11/2000 | Caskey et al. ................. 435/6 |
| 6,177,251 B1 | 1/2001 | Vogelstein et al. ............. 435/6 |

FOREIGN PATENT DOCUMENTS

| | | |
|---|---|---|
| AU | A-11325/95 | 10/1994 |
| EP | 0 185 494 A2 | 6/1986 |
| EP | 0 284 362 A2 | 9/1988 |

(List continued on next page.)

OTHER PUBLICATIONS

Beskin et al., "On the Mechanism of the Modular Primer Effect," *Nucleic Acids Research*, vol. 23, No. 15, pp. 2881–2885 (1995).

(List continued on next page.)

*Primary Examiner*—Jeffrey Fredman
*Assistant Examiner*—Suryaprabha Chunduru
(74) *Attorney, Agent, or Firm*—Testa, Hurwitz & Thibeault, LLP

(57) ABSTRACT

Methods for detecting nucleotide deletions in biological samples are described. Methods of the invention are particulary useful for detecting deletions in regions of polynucleotide repeats. In particular, methods of the invention are useful to detect deletions at the BAT26 locus.

18 Claims, 3 Drawing Sheets

FOREIGN PATENT DOCUMENTS

| | | |
|---|---|---|
| EP | 0 332 435 A2 | 9/1989 |
| EP | 0 337 498 A2 | 10/1989 |
| EP | 0 390 323 A2 | 10/1990 |
| EP | 0 390 323 A3 | 10/1990 |
| EP | 0 407 789 A1 | 1/1991 |
| EP | 0 407 789 B1 | 1/1991 |
| EP | 0 408 918 A1 | 1/1991 |
| EP | 0 332 435 B1 | 4/1992 |
| EP | 0 497 527 A1 | 8/1992 |
| EP | 0 408 918 B1 | 11/1993 |
| EP | 0 608 004 A2 | 7/1994 |
| EP | 0 259 031 B1 | 11/1994 |
| EP | 0 664 339 A1 | 7/1995 |
| GB | 2 293 238 A | 3/1996 |
| WO | WO 89/11211 | 11/1989 |
| WO | WO 90/09455 | 8/1990 |
| WO | WO 91/13075 | 9/1991 |
| WO | WO 92/13103 | 8/1992 |
| WO | WO 92/15712 | 9/1992 |
| WO | WO 92/16657 | 10/1992 |
| WO | WO 93/06240 | 4/1993 |
| WO | WO 93/18186 | 9/1993 |
| WO | WO 93/20233 | 10/1993 |
| WO | WO 93/20235 | 10/1993 |
| WO | WO 94/00603 | 1/1994 |
| WO | WO 94/01447 | 1/1994 |
| WO | WO 94/09161 | 4/1994 |
| WO | WO 94/10575 | 5/1994 |
| WO | WO 94/11383 | 5/1994 |
| WO | WO 94/23055 | 10/1994 |
| WO | WO 95/00669 | 1/1995 |
| WO | WO 95/07361 | 3/1995 |
| WO | WO 95/09928 | 4/1995 |
| WO | WO 95/09929 | 4/1995 |
| WO | WO 95/12606 | 5/1995 |
| WO | WO 95/12607 | 5/1995 |
| WO | WO 95/13397 | 5/1995 |
| WO | WO 95/15400 | 6/1995 |
| WO | WO 95/16792 | 6/1995 |
| WO | WO 95/18818 | 7/1995 |
| WO | WO 95/19448 | 7/1995 |
| WO | WO 95/20680 | 8/1995 |
| WO | WO 95/25813 | 9/1995 |
| WO | WO 95/31728 | 11/1995 |
| WO | WO 96/01907 | 1/1996 |
| WO | WO 96/02671 | 2/1996 |
| WO | WO 96/06951 | 3/1996 |
| WO | WO 96/08514 | 3/1996 |
| WO | WO 96/12821 | 5/1996 |
| WO | WO 96/13611 | 5/1996 |
| WO | WO 96/30545 | 10/1996 |
| WO | WO 97/09449 | 3/1997 |
| WO | WO 97/09600 | 3/1997 |
| WO | WO 97/22719 | 6/1997 |
| WO | WO 97/23651 | 7/1997 |
| WO | WO97/25442 | 7/1997 |
| WO | WO 98/13522 | 4/1998 |
| WO | WO 98/38338 | 9/1998 |
| WO | WO 98/58084 | 12/1998 |

OTHER PUBLICATIONS

Blun H.E., "Colorectal cancer: Future population screening for early colorectal cancer," *European Journal of Cancer*, 31A: 1369–1372, (1995).

Caetano–Anollés "Amplifying DNA with Arbitrary Oligonucleotide Primers," *Cold Spring Harbor Laboratory Press*, ISSN 1054–9803, pp. 85–94 (1993).

Carothers et al., "Point Mutation Analysis in a Mammalian Gene: Rapid Preparation of Total RNA, PCR Amplification of cDNA, and Taq Sequencing by a Novel Method," *494 BioTechniques*, vol. 7, pp. 494–499 (date unknown).

Chen et al. "Template–Directed Dye–Terminator Incorporation (TDI) Assay: A Homogeneous DNA Diagnostic Method Based on Fluorescence Resonance Energy Transfer," *Nucleic Acids Research*, vol. 25, No. 2, pp. 347–353 (1997).

Chen et al., "Fluorescence Energy Transfer Detection as a Homogeneous DNA Diagnostic Method," *Proc. Natl. Acad. Sci.*, vol. 97, pp. 10756–10761 (Sep. 1997).

Exact Laboratories, Inc. "Search Report" (EXT–016PC) (Sep. 13, 1999—date of mailing).

Fu et al., "A DNA Sequencing Strategy That Requires Only Five Bases of Known Terminal Sequence for Priming," *Proc. Natl. Acad. Sci. USA*, 92: pp. 10162–10166 (1995).

Hasegawa et al., "Detection of K–ras mutations in DNAs isolated from feces of patients with colorectal tumors by mutant–allele–specific amplification (MASA)," *Oncogene*, vol. 10, 8 pages (1995).

Ikonen et al., "Quantitative Determination of Rare mRNA Species by PCR and Solid–phase Minisequencing," *Cold Spring Harbor Laboratory Press*, ISSN 1054–8903, pp. 234–240 (1992).

Kieleczawa et al., "DNA Sequencing by Primer Walking with Strings of Contiguous Hexamers," *Science*, 258: pp. 1787–1791 (Dec. 11, 1992).

Kotler et al., (1993) "DNA Sequencing Modular Primers Assembled from a Library of Hexamers or Pentamers," *Proc. Natl. Acad. Sci. USA*, 90: pp. 4241–4245 (May 1993).

Krook et al, "Rapid and simultaneous detection of multiple mutations by pooled and multiplex single nucleotide primer extension: application to the study of insulin–responsive glucose transporter and insulin receptor mutations in non–insulin–dependent diabetes," *Human Molecular Genetics*, vol. 1, No. 6, pp. 391–395 (1992).

Netzer, P. et al., "Screening sigmoidoscopy or colosopy for detection of colorectal adenomas and cancers?" *Gastroenterology*, 112(4), A626, (1997).

Ph Lebacq, "Polymerase chain reaction and other methods to detect hot–spot and multiple gene mutations," *Advances in Clinical Biology*, vol. 50, pp. 709–712 (1992).

Runnobaum et al., "Multiplex PCR Screening detects small p53 deletions and insertions in human ovarian cancer cell lines," *Human Genetics*, vol. 93, pp. 620–624 (1994).

Shumaker et al., "Mutations Detection by Solid Phase Primer Extension," *Human Mutation*, vol. 7, pp. 346–354 (1996).

Syvänen, "Detection of Point Mutations in Human Genes by the Solid–phase Minisequencing Method," *Clinica Chimica Acta*, vol. 226, pp. 225–236 (1994).

Syvänen et al., "Identification of Individuals by Analysis of Biallelic DNA Markers, Using PCR and Solid–Phase Minisequencing," *Am. J. Hum. Gene.*, vol. 52, pp. 46–59 (1993).

Ugozzoli, et al., "Detection of Specific Alleles by Using Allele–Specific Primer Extension Followed by Capture on Solid Support," *GATA* 9(4): pp. 107–112 (1992).

Villa et al., "Identification of subjects at risk for colorectal carcinoma through a test based on k–ras determination in the stool," *Gastroenterology*, 110(5): 1346–1353, (1996).

Boom et al., *"Rapid and Simple Method for Purification of Nucleic Acids,"* *Journal of Clinical Microbiology*, vol. 28, No. 3, pp. 495–503 (1990).

Giacona et al., "Cell–Free DNA in Human Blood Plasma: Length Measurements in Patients with Pancreatic Cancer and Healthy Controls," *Pancreas*, vol. 17, No. 1, pp. 89–97 (1998).

Hollstein et al., "p53 Mutations in Human Cancers," *Science*, vol. 253, pp. 49–53 (Jul. 5, 1991).

Nikiforov et al., "Genetic Bit Analysis: a solid phase method for typing single nucleotide polymorphism," *Nucleic Acids Research*, vol. 22, No. 20, pp. 4167–4175, (1994).

Sidransky et al., "Identification of p53 Gene Mutations in Bladder Cancers and Urine Samples," *Science*, vol. 252, pp. 706–709 (May 1991).

Syvänen, "Solid–Phase Minisequencing," *Detection of Mutations and Polymorphism in DNA*, Chapter 6, pp. 53–64 (1997).

Iwaya et al., "Infrequent Frameshift Mutations of Ploynucleotide Repeats in Multiple Primary Cancers Affecting the Esophagus and Other Organs," *Gene, Chromosomes & Cancer*, vol. 23, pp. 317–322 (1998).

Aaltonen et al. (1994) "Replication Errors in Benign and Malignant Tumors from Hereditary Nonpolyposis Colorectal Cancer Patients" *Cancer Research*, 54: 1645–1648.

Aaltonen et al. (1998) "Incidence of Hereditary Nonpolyposis Colorectal Cancer and the Feasibility of Molecular Screening for the Disease" *The New England Journal of Medicine* 338: 1481–1487.

Ausubel et al., (1995), *Short Protocols in Molecular Biology*, 3d ed., pp. 2–3 –2–12, 3–30 –3–33.

Bertario et al. (1999) "Risk of Colorectal Cancer Following Colonoscopic Polypectomy" *Tumori* 85: 157–162.

Blum H.E., (1995) "Colorectal Cancer: Future Population Screening for Early Colorectal Cancer" *European Journal of Cancer*, vol. 31A, pp. 1369–1372.

Bos et al., (May 28, 1987) "Prevalence of ras Gene Mutations in Human Colorectal Cancers," *Nature*, vol. 327, pp. 293–297.

Caldas et al., (Jul. 1, 1994) "Detection of K–ras Mutations in the Stool of Patients with Pancreatic Adenocarcinoma and Pancreatic Ductal Hyperplasia" *Cancer Research*, vol. 54, pp. 3568–3573.

Capozzi et al. (1999) "Evaluation of the Replication Error Phenotype in Relation to Molecular and Clinicopathological Features in Hereditary and Early Onset Colorectal Cancer" *European Journal of Cancer* 35: 289–295.

Cave et al., (1994) "Reliability of PCR Directly from Stool Samples: Usefulness of an Internal Standard," *BioTechniques*, vol. 16, No. 5, pp. 809–810.

Chapelle (1999) "Testing Tumors for Microsatellite Instability" *European Journal of Human Genetics* 7: 407–408.

Charlesworth et al., (Sep. 15, 1994) "The Evolutionary Dynamics of Repetitive DNA in Eukaryotes," *Nature*, vol. 371, pp. 215–220.

Chen et al. (1997) "Microsatellite Instability in Sporadic-Colon–Cancer Patients With and Without Liver Metastases" *International Journal of Cancer* 74: 470–474.

Coll et al., (Oct. 1989) "Evaluation of a Rapid Method of Extracting DNA from Stool Samples for Use in Hybridzation Assays," *Journal of Clinical Microbiology*, vol. 27, No. 10, pp. 2245–2248.

Coughlin et al. (1999) "Public Health Perspectives on Testing for Colorectal Cancer Susceptibility Genes" *American Journal of Preventive Medicine* 16: 99–104.

Cunningham C. and M.G. Dunlop, (1996) "Molecular Genetic Basis of Colorectal Cancer Susceptibility," *British Journal of Surgery*, vol. 83, pp. 321–329.

Deng et al., (Dec. 20, 1996 ) "Loss of Heterozygosity in Normal Tissue Adjacent to Breast Carcinomas," *Science*, vol. 274, pp. 2057–2059.

Deuter et al., (1995) "A Method for Preparation of Fecal DNA Suitable for PCR," *Nucleic Acids Research*, vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now by Used for Early Diagnosis of Malignancy?" *Clin. Chem,.* vol. 41, No. 10, pp. 1410–1413.

Eguchi et al., (Apr. 15, 1996) "Mutations of the p53 Gene in the Stool of Patients with Resectable Colorectal Cancer," *Cancer Supplement*, vol. 77, No. 8, pp. 1707–1710.

Enari et al., (Jan. 1, 1998) "A Caspase–Activated DNase that Degrades DNA During Apoptosis, and its Inhibitor ICAD," *Nature*, vol. 391, pp. 43–50.

Fearon, E.R., (1995) "16 Molecular Abnormalities in Colon and Rectal Cancer," *The Molecular Basis of Cancer*, pp. 340–357.

Grossman et al. (1988), "Colonoscopic Screening of persons With Suspected Risk Factors for Colon Cancer" *Gastroenterology* 94: 395–400.

Gyllensten U. B., Allen M., (1995) "Sequencing of In Vitro Amplified DNA," *Recombinant DNA Methodology II*, (Wu, ed.), pp. 565–578.

Hasegawa et al., (1995) "Detection of K–ras Mutations in DNAs Isolated From Feces of Patients with Colorectal Tumors by Mutant–Allele–Specific Amplification (MASA)," *Oncogene*, vol. 10, pp. 1441–1445.

Hoang et al. (1997) "BAT–26, an Indicator of the Replication Error Phenotype in Colorectal Cancers and Cell Lines" *Cancer Research* 57: 300–303.

Honchel et al., (1995) "Genomic Instability in Neoplasia," *Seminars in Cell Biology*, vol. 6, pp. 45–52.

Hoss et al., (Sep. 17, 1992) "Excrement Analysis by PCR" *Scientific Correspondence* pp. 199.

Iino et al. (1999) "DNA Microsatellite Instability in Hyperplastic Polyps, Serrated Adenomas, and Mixed Polyps: a Mild Mutator Pathway for Colorectal Cancer?" *Journal of Clinical Pathology* 52: 5–9.

Iniesta et al. (1998) "Genetic Abnormalities and Microsatellite Instability in Colorectal Cancer" *Cancer Detection and Prevention* 22: 383–395.

Ishimaru et al. (1995) "Microsatellite Instability in Primary and Metastatic Colorectal Cancers" *International Journal of Cancer* 64: 153–157.

Jarvinen et al. (1995) "Screening Reduces Colorectal Cancer Rate in Families With Hereditary Nonpolyposis Colorectal Cancer" *Gastroenterology* 108: 1405–1411.

Jernvall et al. (1999) "Microsatellite Instability: Impact on Cancer Progression in Proximal and Distal Colorectal Cancers" *European Journal of Cancer* 35: 197–201.

Jessup J.M. and G.E. Gallick, (Sep./Oct. 1992) "The Biology of Colorectal Carcinoma," *Current Problems in Cancer* pp. 263–328.

Jonsson et al., (Jan. 1995) "From Mutation Mapping to Phenotype Cloning," *Proc. Natl. Acad. Sci.*, vol. 92 pp. 83–85.

Kim et al. (1998) "Microsatellite Instability in Young Patients With Colorectal Cancer" *Pathology International* 48: 586–594.

Konishi et al. (1996) "Molecular Nature of Colon Tumors in Hereditary Nonpolyposis Colon Cancer, Familial Polyposis, and Sporadic Colon Cancer" *Gastroenterology* 111: 307–317.

Lamberti et al. (1999) "Microsatellite Instability—a Useful Diagnostic Tool to Select Patients at High Risk for Hereditary Non–Polyposis Colorectal Cancer: A Study in Different Groups of Patients With Colorectal Cancer" *Gut* 44: 839–843.

Lengauer et al., (Dec. 17, 1998) "Genetic Instabilities in Human Cancers," *Nature*, vol. 396, pp. 643–649.

Leong et al., (1993) "Detection of MYCN Gene Amplification and Deletions of Chromosome 1p in Neuroblastoma by In Situ Hybridization Using Routine Histologic Sections," *Laboratory Investigations*, vol. 69, No. 1, pp. 43–50.

Lin et al. (1998) "Colorectal and Extracolonic Cancer Variations in MLH1/MSH2 Hereditary Nonpolyposis Colorectal Cancer Kindreds and the General Population" *Diseases of the Colon & Rectum* 41: 428–433.

Litia et al., (1992) "Simultaneous Detection of Two Cystic Fibrosis Alleles Using Dual–Label Time–Resolved Fluorometry," *Molecular and Cellular Probes*, vol. 6, pp. 505–512.

Lleonart et al. (1998) "Microsatellite Instability and p53 Mutations in Sporadic Right and Left Colon Carcinoma" *American Cancer Society* 83: 889–895.

Loktionov A. and I. K. O'Neill, (1995) "Early Detection of Cancer–Associated Gene Alterations in DNA Isolated from Rat Feces During Intestinal Tumor Induction with 1,2–Dimethylhydrazine," *International Journal of Oncology*, vol. 6, pp. 437–445.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337–341.

Mao L. et al., (Feb. 2, 1996) "Molecular Detection of Primary Bladder Cancer by Microsatellite Analysis," *Science*, vol. 271, pp. 659–662.

Myers, R.M., (Feb. 12, 1993) "The Pluses of Subtraction," *Science*, vol. 259, pp. 942–943.

Naber S. P., (Dec. 1, 1994) "Molecular Pathology—Detection of Neoplasia," *New England Journal of Medicine*, vol. 331, No. 22, pp. 1508–1510.

Nollau et al., (May 1996) "Isolation of DNA from Stool and Bodily Fluids for PCR Amplication," *BioTechniques*, vol. 20, No. 5, pp. 784–788.

Nollau et al., (1996) "Detection of K–ras Mutations in Stools of Patients with Colorectal Cancer by Mutant–Enriched PCR," *Int. J. Cancer*, vol. 66 pp. 332–336.

Orlow I., et al., (Oct. 18, 1995) "Deletion of the p16 and p15 Genes in Human Bladder Tumors *Journal of the National Cancer Institute*, ," vol. 87, No. 20, pp. 1524–1529.

Park et al. (1999) "Gene–Environment Interaction in Hereditary Nonpolyposis Colorectal Cancer with Implications for Diagnosis and Genetic Testing" *International Journal of Cancer* 82: 516–519.

Peltomaki et al. (1997) "Mutations Predisposing to Hereditary Nonpolyposis Colorectal Cancer: Database and Results of a Collaborative Study" *Gastroenterology* 113: 1146–1158.

Pharmacia, (1998) *BioDirectory*, pp. 104–109.

Pharmacia, (1991/1992) *Molecular and Cell Biology Catalogue*, pp. 8.3–8.6.

Piao et al., (Sep. 1997) "Relationship between Loss of Heterozygosity of Tumor Suppressor Genes and Histologic Differentiation in Hepatocellular Carcinoma," *Cancer*, vol. 80, No. 5, pp. 865–872.

Ponz de Leon et al. (1998) "Frequency and Type of Colorectal Tumors in Asymptomatic High –Risk Individuals in Families with Hereditary Nonpolyposis Colorectal Cancer" *Cancer Epidemiology, Biomarkers & Prevention* 7: 639–641.

Ponz de Leon et al. (1999) "Hereditary Colorectal Cancer in the General Population: From Cancer Registration to Molecular Diagnosis" *Gut* 45: 32–38.

Pyatt et al. (1999) "Polymorphic Variation at the BAT–25 and BAT–25 and BAT–26 Loci in Indviduals of African Origin" *American Journal of Pathology* 155: 349–353.

Raff, M., (Nov. 12, 1998) "Cell Suicide for Beginners," *Nature*, vol. 396, pp. 119–122.

Rashid et al. (1999) "Genetic Epidemiology of Mutated K–ras Proto–Oncogene, Altered Suppressor Genes, and Microsatellite Instability in Colorectal Adenomas" *Gut* 44: 826–833.

Ravelingien et al., (1995) "Contribution of Molecular Oncology in the Detection of Colorectal Carcinomas," *Acta Gastro–Enterologica Belgica*, vol. 58, pp. 270–273.

Riegler et al. (1999) "Prevalence of HNPCC in a Series of Consecutive Patients on the First Endoscopic Diagnosis of Colorectal Cancer: A Multicenter Study" *Endoscopy* 31: 337–341.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240–251.

Ridanpaa et al., (1995) "Detection of Loss of Heterozygosity in the p53 Tumor Suppressor Gene Using a PCR–based Assay," *Path. Res. Pract.*, vol. 191, pp. 399–402.

Rodriquez–Bigas et al. (1997) "A National Cancer Institute Worship on Hereditary Nonpolyposis Colorectal Cancer Syndrome: Meeting Highlights and Bethesda Guidelines" *Journal of the National Cancer Institute* 89: 1758–1762.

Salahshor et al. (1999) "Microsatellite Instability in Sporadic Colorectal Cancer is Not an Independent Prognostic Factor" *British Journal of Cancer* 81: 190–193.

Samowitz et al. (1995) "Microsatellite Instability in Human Colonic Cancer Is Not a Useful Clinical Indicator of Familial Colorectal Cancer" Gastroenterology 109: 1765–1771.

Samowitz et al. (1997) "Microsatellite Instability in Colorectal Adenomas" *Gastroenterology* 112: 1515–1519.

Samowitz et al. (1999) "BAT–26 and BAT–40 Instability in Colorectal Adenomas and Carcinomas and Germline Polymorphisms" *American Journal of Pathology* 154: 1637–1641.

Sanger et al., (Dec. 1977) "DNA Sequencing with Chain–Terminating Inhibitors" *Proc. Natl. Acad. Sci. USA*, vol. 74, No. 12, pp. 5463–5467.

Segel I., (1976), "Double Label Analysis," *Biochemical Calculations*, 2d ed., pp. 373–376.

Sidransky, et al., (Apr. 3, 1992) "Identification of ras Oncogene Mutations in the Stool of Patients with Curable Colorectal Tumors," *Science*, vol. 256, pp. 102–105.

Smith–Ravin et al., (1995) "Detection of c–Ki–ras Mutations in Faecal Samples from Sporadic Colorectal Cancer Patients," *Gut*, vol. 36, pp. 81–86.

Syngal et al. (1998) "Benefits of Colonoscopic Surveillance and Prophylactic Colectomy in Patients With Hereditary Nonpolyposis Colorectal Cancer Mutations" *Annals of Internal Medicine* 129: 787–796.

Syngal et al. (1999) "Interpretation of Genetic Test Results for Hereditary Nonpolyposis Colorectal Cancer" *JAMA* 282: 247.

Takeda et al., (1993) "Detection of K–ras Mutation in Sputum by Mutant–Allele–Specific Amplification (MASA)," *Human Mutation*, vol. 2, pp. 112–117.

Thibodeau et al., (May 7, 1993) "Microsatellite Instability in Cancer of the Proximal Colon," *Science*, vol. 260, pp. 816–819.

Vasen et al. (1993) "Surveillance in Hereditary Nonpolyposis Colorectal Cancer: An International Cooperative Study of 165 Families" *Diseases of the Colon & Rectum*) 36: 1–4.

Vasen et al. (1998) "A Cost–Effectiveness Analysis of Colorecta Screening of Hereditary Nonpolyposis Colorectal Carcinoma Gene Carriers" *American Cancer Society* 82: 1632–1637.

Vasen et al. (1999) "New Clinical Criteria for Hereditary Nonpolyposis Colorectal Cancer (HNPCC, Lynch Syndrome) Proposed by the International Collorabotative Group on HNPCC" *Gastroenterology* 116: 1453–1456.

Villa et al., (May 1996) "Identification of Subjects at Risk for Colorectal Carcinoma Through a Test Based on K–ras Determination in the Stool," *Gastroenterology*, vol. 110, No. 5, pp. 1346–1353.

Vogelstein, B. and Kinzler, K.W., (Aug., 1999) "Digital PCR," *Proc. Natl. Acad. Sci. USA*, vol. 96, pp. 9236–9241.

Wallace et al., (1979) "Hybridization of Synthetic Oligodeoxyribonucleotides to Φχ 174 DNA: the Effect of Single Base Pair Mismatch," *Nucleic Acids Research*, vol. 6, No. 11, pp. 3543–3557.

Walsh et al., (Feb. 6, 1992) "Preferential PCR Amplificaiton of Alleles: Mechanisms and Solutions," *PCR Methods and Applications*, pp. 241–250.

Wang et al., (May 15, 1998) "Large–Scale Identification, Mapping, and Genotyping of Single–Nucleotide Olymorphisms in the Human Genome," *Science*, vol. 280, pp. 1077–1082.

Watson et al., "Isolation of Differentiality Expressed Sequence Tags from Human Breast Cancer," *Advances in Brief XP 000576043*, pp. 4598–4602.

Wijnen et al. (1999) "Familial Endometrial Cancer in Female Carriers of MSH6 Germline Mutations" *Nature Genetics* 23: 142–144.

Young G.P., and B.H. Demediu, (1992) "The Genetics, Epidemiology, and Early Detection of Gastrointestinal Cancers" *Current Opinion in Oncology*, vol. 4, pp. 728–735.

Zhou et al. (1997) "Allelic Profiles of Mononucleotide Repeat Microsatellites in Control Individuals and in Colorectal Tumors With and Without Replication Errors" *Oncogene* 15: 1713–1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21: 101–107.

Lipkin et al., (1998) "Quantitative Trait Locus Mapping in Dairy Cattle by Means of Selective Milk DNA Pooling Using Dinucleotide Microsatellite Markers: Analysis of Milk Protein Percentage" *Genetics* 49: 1557–1567.

Walsh et al., (1996) "Sequence Analysis and Characterization of Stutter Products at the Tetranucleotide Repeat Locus vWA" *Nucleic Acids Research* vol. 24, No. 14 2807–2812.

Perlin et al., (1995) "Toward Fully Automated Tenotyping: Genotyping Microsatellite Markers by Deconvolution" *American Journal of Human Genetics* 57: 1199–1210.

Miller et al. (1997) "Semiautomated Resolution of Overlapping Stutter Patterns in Genomic Microsatellite Analysis" *Analytical Biochemistry* 251: 50–56.

Andreas Braun et al., "Improved Analysis of Microsatellites Using Mass spectrometry" *Genomics*, (1997) vol. 46, pp. 18–23.

Ragnhild A. Lothe, et al., "The APC Gene I1307K Variant is Rare in Norwegian Patients with Familial and Sporadic Colorectal or Breast Cancer" *Cancer Research*, (Jul. 15, 1998), vol. 58, pp. 2923–2324.

Gismondi Viviana et al., "Characterization of 19 Novel and Sic Recurring APC Mutations in Italian Adenomatous Polyposis Patients, Using Two Different Mutation Detection Techniques" *Human Mutation* (1997) vol. 9, No. 4, pp. 370–373.

Frangi D et al. Nonsense mutations affect C1 inhibitor messanger RNA levels in patients with Type I hereditary angioneurotic edema. J.Clin.Inves., 88(3): 755–759, 1991.*

Sambrook J et al. Molecular cloning. Second edition, p. 13.67–13.69, 1989.*

* cited by examiner

METHODS FOR DETECTING MUTATIONS USING PRIMER EXTENSION

REFERENCE TO RELATED APPLICATION

This application is a continuation of U.S. Ser. No. 09/371,991, filed Aug. 11, 1999 is now U.S. Pat. No. 6,280,947, the disclosure of which is herein incorporated by reference.

FIELD OF THE INVENTION

The invention relates generally to methods for detecting nucleic acid mutations in biological samples, and more specifically to methods for detecting nucleic acid deletions or insertions using primer extension reactions.

BACKGROUND OF THE INVENTION

Numerous diseases are thought to be initiated by disruptions in genomic stability. For example, sickle cell anemia, phenylketonuria, hemophilia, cystic fibrosis, and various cancers have been associated with one or more genetic mutation(s). Increased knowledge of the molecular basis for disease has lead to a proliferation of screening assays capable of detecting disease-associated nucleic acid mutations.

One such method identifies a genomic region thought to be associated with a disease and compares the wild-type sequence in that region with the sequence in a patient sample. Differences in the sequences constitute a positive screen. See e.g., Engelke, et al, Proc. Natl. Acad. Sci., 85: 544–548 (1988). Such methods are time-consuming, costly, and often results in an inability to identify the mutation of interest. Thus, sequencing is not practical for large-scale screening assays.

A variety of detection methods have been developed which exploit sequence variations in DNA using enzymatic and chemical cleavage techniques. A commonly-used screen for DNA polymorphisms consists of digesting DNA with restriction endonucleases and analyzing the resulting fragments by means of Southern blots, as reported by Botstein et al.,Am. J. Hum. Genet., 32: 314–331 (1980) and White et a., Sci. Am., 258: 40–48 (1988). Mutations that affect the recognition sequence of the endonuclease will preclude enzymatic cleavage at that site, thereby altering the cleavage pattern of the DNA. Sequences are compared by looking for differences in restriction fragment lengths. A problem with this method (known as restriction fragment length polymorphism mapping or RFLP mapping) is its inability to detect mutations that do not affect cleavage with a restriction endonuclease. One study reported that only 0.7% of the mutational variants estimated to be present in a 40,000 base pair region of human DNA were detected using RFLP analysis. Jeffreys, Cell, 18: 1–18 (1979).

Single-base mutations have been detected by differential hybridization techniques using allele-specific oligonucleotide probes. Saiki et al,Proc. Natl. Acad. Sci., 86: 6230–6234 (1989). Mutations are identified on the basis of the higher thermal stability of the perfectly-matched probes as compared to mismatched probes. Disadvantages of this approach for mutation analysis include:(1) the requirement for optimization of hybridization for each probe, and (2) the nature of the mismatch and the local sequence impose limitations on the degree of discrimination of the probes. In practice, tests based only on parameters of nucleic acid hybridization function poorly when the sequence complexity of the test sample is high (e.g., in a heterogeneous biological sample). This is partly due to the small thermodynamic differences in hybrid stability generated by single nucleotide changes. Therefore, nucleic acid hybridization is generally combined with some other selection or enrichment procedure for analytical and diagnostic purposes.

A number of detection methods have been developed which are based on template-dependent, primer extension. Those methods can be placed into one of two categories: (1) methods using primers which span the region to be interrogated for the mutation, and (2) methods using primers which hybridize upstream of the region to be interrogated for the mutation.

In the first category, U.S. Pat. No. 5,578,458 reports a method in which single base mutations are detected by competitive oligonucleotide priming under hybridization conditions that favor the binding of a perfectly-matched primer as compared to one with a mismatch. U.S. Pat. No. 4,851,331 reports a similar method in which the 3' terminal nucleotide of the primer corresponds to the variant nucleotide of interest. Since mismatching of the primer and the template at the 3' terminal nucleotide of the primer inhibits elongation, significant differences in the amount of incorporation of a tracer nucleotide result under normal primer extension conditions.

Methods in the second category are based on incorporation of detectable, chain-terminating nucleotides in the extending primer. Such single nucleotide primer-guided extension assays have been used to detect aspartylglucosaminuria, hemophilia B, and cystic fibrosis; and for quantifying point mutations associated with Leber Hereditary Optic Neuropathy. See. e.g., Kuppuswamy et al., Proc. Natl. Acad. Sci. USA, 88: 1143–1147 (1991); Syvanen et al., Genomics,8: 684–692 (1990); Juvonen et al., Human Genetics, 93: 16–20 (1994); Ikonen et al., PCR Meth. Applications, 1: 234–240 (1992); Ikonen et al, Proc. Natl. Acad. Sci. USA, 88: 11222–11226 (1991); Nikiforov et al., Nucleic Acids Research, 22: 4167–4175 (1994). An alternative primer extension method involving the addition of several nucleotides prior to the chain terminating nucleotide has also been proposed in order to enhance resolution of the extended primers based on their molecular weights. See e.g., Fahy et al., WO/96130545 (1996).

Strategies based on primer extension require considerable optimization to ensure that only the perfectly annealed oligonucleotide functions as a primer for the extension reaction. The advantage conferred by the high fidelity of the polymerases can be compromised by the tolerance of nucleotide mismatches in the hybridization of the primer to the template. Any "false" priming will be difficult to distinguish from a true positive signal. The reaction conditions of a primer extension reaction can be optimized to reduce "false" priming due to a mismatched oligonucleotide. However, optimization is labor intensive and expensive, and often results in lower sensitivity due to a reduced yield of extended primer.

A number of mutations leading to various forms of cancer involve the deletion of multiple nucleotides from a genomic sequence. An example is the BAT26 segment of the MSH2 mismatch repair gene. The BAT26 segment contains a long poly-A tract. In certain cancers, a characteristic 5 base pair deletion occurs in the poly-A tract. Detection of that deletion may provide diagnostic information. Accordingly, the invention provides methods for detecting deletions in genomic regions, such as BAT26 and others, which may be associated with disease.

SUMMARY OF THE INVENTION

Methods of the invention provide assays for identification of a deletion in a genomic region suspected to be indicative of disease. In general, methods of the invention comprise annealing a primer upstream of a region in which a deletion is suspected to occur, extending the primer through the region, terminating extension at a known end-point, and comparing the length and/or weight of the extended primer with that of an extended primer from the corresponding willd-type (non-affected) region or a molecular weight standard (either known or run in parallel). In preferred embodiments, the extended primer is labeled downstream of the region suspected to be deleted. In a highly-preferred embodiment, the comparative length and/or molecular weight of the extended primer is determined by gel electrophoresis or mass spectroscopy. Also in a highly-preferred embodiment, the region suspected to contain the deletion comprises a poly-nucleotide tract in which the deletion is suspected to occur, and the sequence immediately downstream of the region is known and does not repeat a nucleotide species present in the polynucleotide tract. Preferably, the polynucleotide tract comprise three, two, or preferably one, species of nucleotide as explained in detail below. Methods of the invention retain the specificity of primer extension assays while increasing their sensitivity by reducing background due to premature termination of the extension reaction. Therefore, methods of the invention provide a highly sensitive and highly specific assay for detecting a small amount of mutant nucleic acid in a heterogeneous sample of predominantly wild-type nucleic acid.

Methods of the invention provide screening assays for the detection of a deletion in a region of the genome comprising one, but no more than three, species of nucleotide, and that is characterized by having a sequence for primer hybridization immediately upstream, and a sequence immediately downstream that does not contain a nucleotide present in the region suspected to be deleted. In a preferred embodiment, methods of the invention comprise selecting a nucleic acid having a known wild-type sequence and having a region (the deletion of which is suspected in disease) comprising at most three different types of nucleotides; hybridizing an oligonucleotide primer, or pair of oligonucleotide primers, immediately upstream of the target region; extending the primer by using a polymerase in the presence of the nucleotide bases that are complementary to the nucleotide bases of the target region, thereby to form a primer extension product; further extending the primer extension product in the presence of a labeled nucleotide that is complementary to a nucleotide base downstream from the target region, but not complementary to a nucleotide base within the target region; and determining the size of the extension product compared to a standard (e.g., a wild-type product or a molecular weight standard).

In a preferred embodiment, the target region in which the deletion is suspected to occur is greater than five nucleotides long, and/or the deletion is great than three nucleotides long. In a preferred embodiment, the primer extension reactions are cycled by varying the reaction temperature through successive annealing, extending and denaturing temperatures. Preferably, the molecular weight standard is the wild-type extension product, or one that corresponds to the expected size for the extension product from the wild-type nucleic acid template. The presence of an extension product smaller than the molecular weight standard is indicative of the presence of a deletion in the target region of the nucleic acid template. In a preferred embodiment, the primer extension product is terminated by incorporating a terminator nucleotide that is complementary to a nucleotide downstream from the target region in a wild type nucleic acid, but not complementary to any of the nucleotides of the target region. In a more preferred embodiment, the labeled nucleotide and the terminator nucleotide are the same. In an alternative embodiment, more than one labeled nucleotide base is incorporated into the extension product prior to incorporation of the terminator nucleotide. Preferably, the nucleotides incorporated during extension through the region suspected of containing a deletion are unlabeled. However, if those nucleotides are labeled, they are preferably distinguishable from the labeled nucleotide that is incorporated at the 3' end of the extension product.

In a preferred embodiment, methods of the invention comprise detecting a nucleic acid mutation in a biological sample, such as stool, urine, semen, blood, sputum, cerebrospinal fluid, pus, or aspirate, that contains a heterogeneous mixture of nucleic acid having a deletion in the target region and wild type nucleic acid. Such a deletion in the target region may be present in only about 1-5% of the nucleic acid molecules having the target region. To increase the sensitivity of the assay, the sample may comprise a polymerase chain reaction product. Method of the invention are particularly useful in analyzing a deletion in the target region that is indicative of the presence of cancerous or precancerous tissue in such a biological sample, including colorectal cancer or precancer detection in stool.

In another embodiment, methods of the invention comprise further extending the primer extension product in the presence of labeled and unlabled nucleotides, the nucleotides being of the same type (i.e., A, T, C, or G) and being complementary to one or more nucleotide downstream from the target region but not complementary to a nucleotide within the target region. In one embodiment the ratio of the labeled nucleotide to unlabeled nucleotide is 1:1. Methods of the invention may also include incorporating more than one monomer of the labeled nucleotide or unlabeled nucleotide into the extension product.

In another embodiment, methods of the invention comprise detecting a deletion in a sample by selecting a nucleic acid with a known wild-type sequence and having a target region suspected of containing a deletion, wherein the target region contains at most three different types of nucleotide bases selected from the group consisting of dGTP, dATP, dTTP, and dCTP; hybridizing an oligonucleotide primer to a region upstream of said target region, in a nucleic acid sample; contacting said hybridized oligonucleotide primer with an extension reaction mixture comprising:i) nucleotides which are complementary to the nucleotides in the target region, ii) a labeled nucleotide which is complementary to a nucleotide found downstream from the target region, but which is not complementary to any nucleotide base found within the target region, and iii) a terminator nucleotide which is complementary to a nucleotide found downstream from the target region, but which is not complementary to any nucleotide found in the target region; extending the hybridized oligonucleotide primer to generate a labeled extension product; and comparing the size of the labeled extension product from step d) to a molecular weight standard, wherein a labeled extension product smaller than the molecular weight standard is indicative of the presence of a deletion in the target region.

Methods of the invention are especially useful to detect indicia of cancer or precancer in a heterogeneous sample. Stool is a good example of a heterogeneous sample in which methods of the invention are useful. A typical stool sample contains patient nucleic acids, but also contains heterologous nucleic acids, proteins, and other cellular debris consistent with the lytic function of the various nucleases, proteinases and the like found in the colon. Under normal circumstances, stool solidifies as it proceeds from the proximal colon to the distal colon. As the solidifying stool passes through the colon, colonic epithelial cells are sloughed onto the stool. If a patient has a developing tumor or adenoma, cells from the tumor or adenoma will also be sloughed onto stool. Those cells, and/or their debris, will contain molecular indicia of disease (e.g., mutations or loss of heterozygosity). In the early stages of development, nucleic acid indicative of an adenoma or tumor comprise only about 1% of the nucleic acid in a voided stool. If left untreated, proportionately more disease-related nucleic acids are found in stool. Methods of the invention are useful for detecting early-stage lesions in heterogeneous samples such as stool. Methods of the invention result in a high degree of sensitivity and specificity for the detection of early-stage disease. Methods of the invention are especially useful in detecting, for example, adenomas in the colon. Adenomas are non-metastatic lesions that frequently have the potential for metastasis. If all adenomas in a patient are detected and removed, the probability of complete cure is virtually certain.

Deletions in the BAT26 locus of the MSH2 mismatch repair gene have been associated with colorectal cancer. Thus, in a highly-preferred embodiment, the region in which a deletion is suspected to occur is the BAT26 locus. That locus contains a polyA tract in which deletions have been associated with cancer or precancer. Use of methods of the invention on the BAT26 locus identifies the characteristic deletions by producing an extension product in affected DNA that is shorter than the expected wild-type extension product. Methods of the invention will be exemplified below using the BAT26 locus. However, methods of the invention are appreciated to be useful on any genetic locus in which a deletion occurs. Especially useful loci are those indicative of disease, and especially cancer.

A detailed description of certain preferred embodiments of the invention is provided below. Other embodiments of the invention are apparent upon review of the detailed description that follows.

DETAILED DESCRIPTION OF THE INVENTION

Figure 1A:
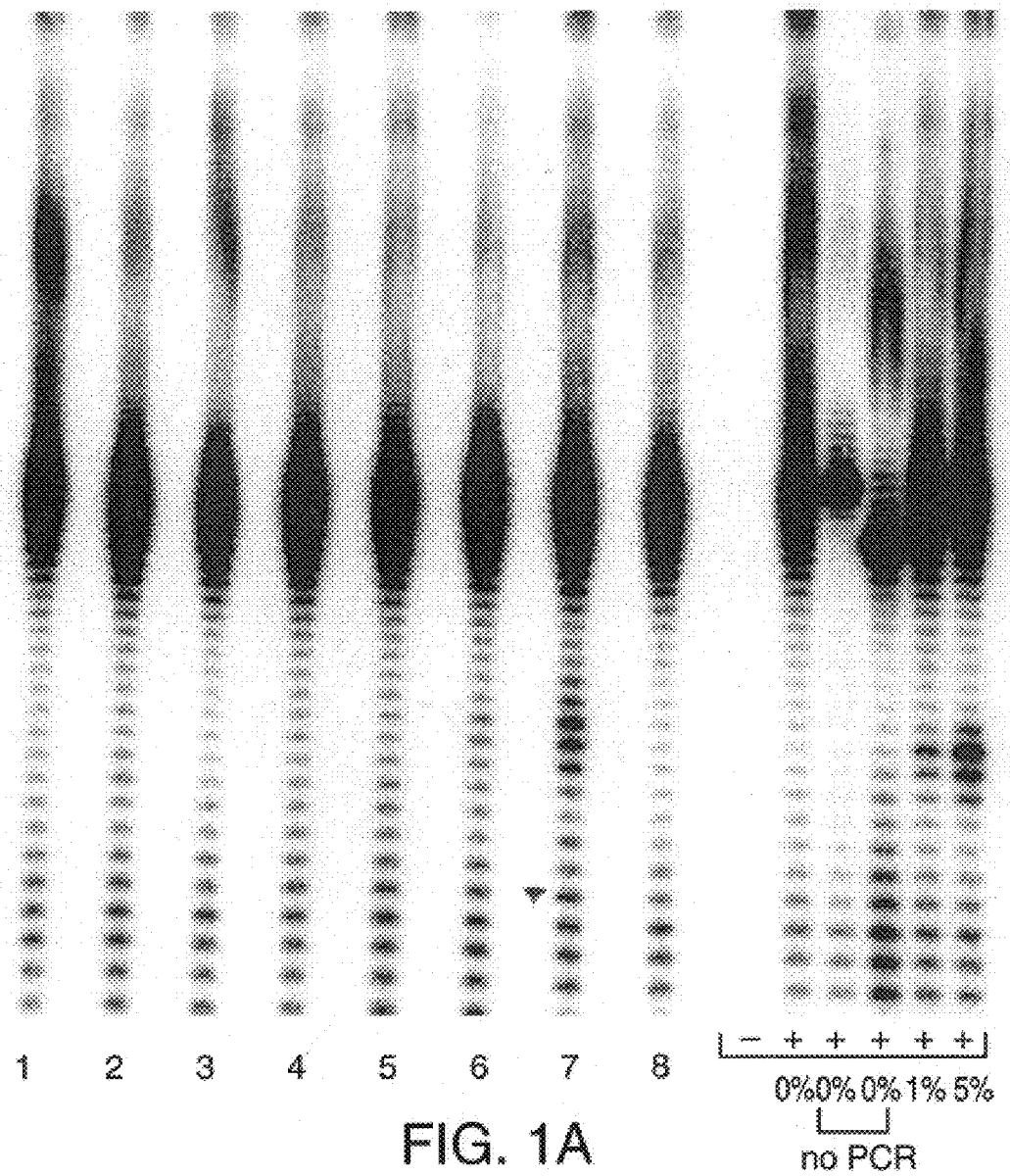
FIG. 1A shows BAT26 deletion detection using primer extension reactions that incorporate labeled bases before the 3' end of the extension product.

Methods of the invention provide highly sensitive assays for detecting the presence of mutations in nucleic acid samples. Methods of the invention are especially useful for detecting the presence of nucleic acid deletions and/or insertions in heterogeneous biological samples. In preferred embodiments, methods of the invention are useful to detect mutations at loci that are associated with a disease such as cancer.

In general, methods of the invention comprise identifying a target nucleic acid region that is suspected of being mutated, and interrogating the target region using a primer extension reaction. A primer is hybridized upstream of the target region and extended through the target region. The extension reaction is terminated at a site beyond the target region. The extension product is analyzed, and the size of the product is used as an indicator of the presence or absence of a mutation in the target nucleic acid region. In general, the presence of an extension product that is smaller than expected is indicative of the presence of a deletion in the target region. Conversely, the presence of a labeled extension product that is larger than expected is generally indicative of the presence of an insertion in the target region. However, the presence of a small or large labeled extension product can also be an indicator of a point mutation in the target region, as explained in greater detail in the following sections.

Methods of the invention are particularly useful when the target region contains a sequence that causes the extending polymerase to pause, stutter, or terminate prematurely. For example, regions containing nucleotide repeats such as a tract of a given nucleotide (such as the polyA tract at the BAT26 locus) dinucleotide or trinucleotide repeats. However, the invention is generally useful to detect mutations at loci having a known wild-type nucleic acid.

In a preferred embodiment, a primer is hybridized upstream of a target region that contains at most three different nucleotide bases. The hybridized primer is extended through the target region in the presence of unlabeled nucleotides that are complementary to nucleotides of the target region. The primer extension product is further extended in the presence of a labeled terminator nucleotide that is complementary to a nucleotide found downstream from the target region, but not found in the target region. An extension product is only labeled if the labeled terminator nucleotide is incorporated in the extension reaction. Consequently, an extension product is only labeled if it is extended through the target region, and along to the template nucleotide that is complementary to the labeled terminator nucleotide.

Accordingly, prematurely terminated extension products are not labeled and do not interfere with the detection and analysis of labeled product by gel electrophoresis and autoradiography.

The present invention comprises embodiments wherein the primer is labeled, or wherein a labeled nucleotide is incorporated into the extension product before extension through the target region is complete, provided that an additional label is incorporated into fully extended products so that they can be distinguished from prematurely terminated extension products. In one embodiment, a primer is labeled with a first label, the labeled primer is hybridized upstream of the target region and extended through the target region, a second label is incorporated into the extension product downstream from the target region, and the extension reaction is terminated. Consequently, an extension product that terminates prematurely within the target region only contains the first label, whereas a fully extended product contains both the first and second label. Accordingly, diagnostically relevant extension products are those that contain both labels.

Methods of the invention also comprise assays in which the extension product is labeled and terminated in separate steps, after extension through the target region is complete. In one embodiment, a template nucleic acid comprises a target region consisting of a repeat of a first nucleotide base. Downstream from the target region is a second nucleotide base followed by a third nucleotide base. A primer is hybridized upstream of the target region and extended through the target region in the presence of unlabeled nucleotides that are complementary to the first nucleotide.

After extension through the target region is complete, the extension product is further extended in the presence of a labeled nucleotide that is complementary to the second nucleotide of the template. Finally, the labeled extension product is terminated via an extension reaction in the presence of a terminator nucleotide (such as a dideoxy nucleotide) that is complementary to the third nucleotide of the template. Other embodiments of this aspect of the invention are also described in the following sections.

Figure 1B:
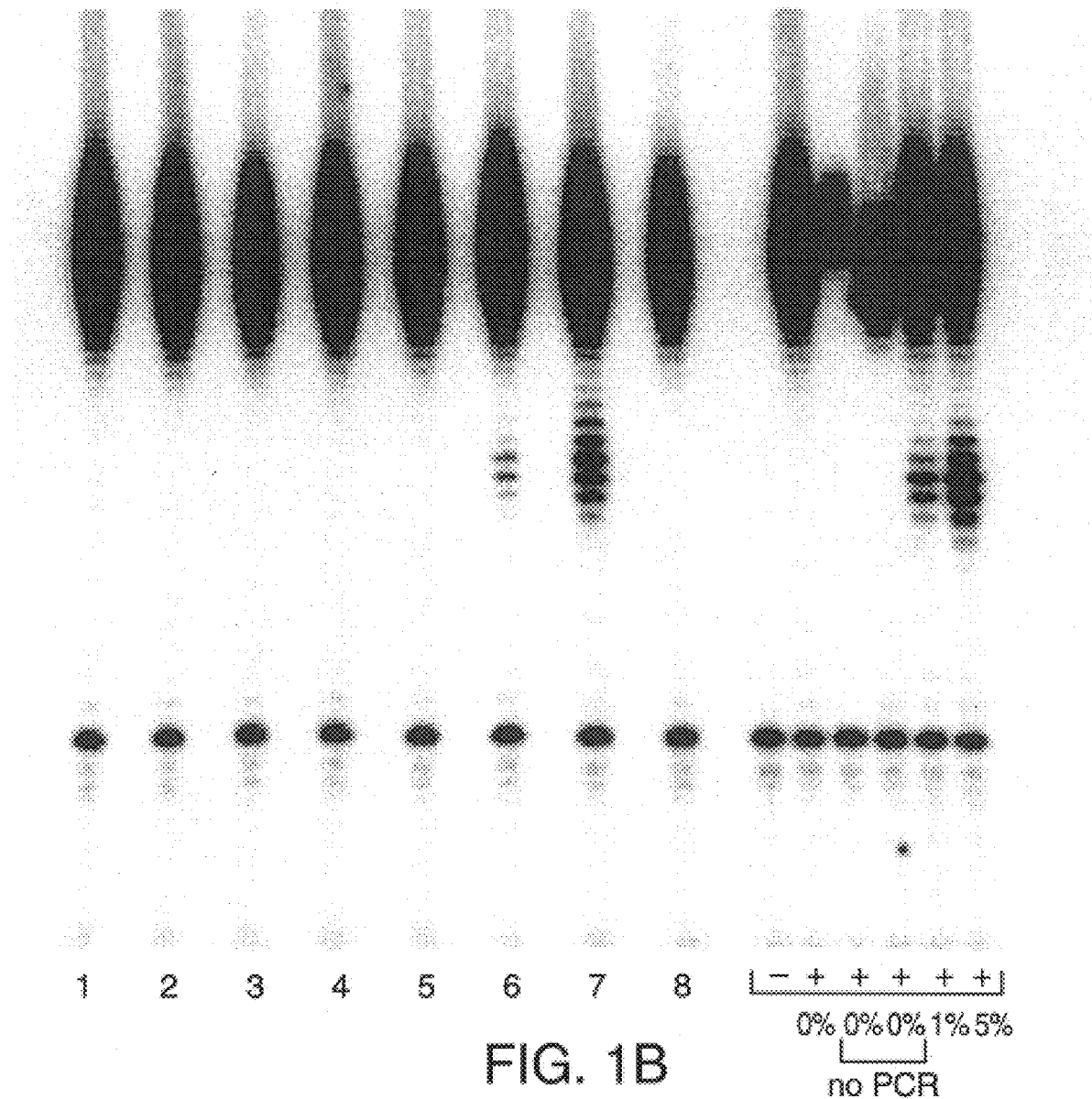
FIG. 1B shows BAT26 deletion detection using primer extension reactions that incorporate labeled bases at the 3' end of the extension product.

Accordingly, an important aspect of the invention is a primer extension reaction wherein prematurely terminated extension products can be distinguished from complete extension products that have not undergone premature termination. Preferably, prematurely terminated extension products are not labeled, whereas complete extension products are detectably labeled. FIG. 1 illustrates the usefulness of the invention in a deletion detection assay. The experimental details relating to FIG. 1 are described in greater detail in Example 1. FIG. 1 show that the invention provides an effective method for minimizing background when interrogating a target nucleic acid region suspected of containing a deletion. FIG. 1A shows multiple samples that were analyzed by a primer extension assay that incorporated labeled nucleotides into the extension product upstream of the target region. In FIG. 1B, the same samples were analyzed according to methods of the invention. FIG. 1B does not contain the background of labeled prematurely terminated extension products that are seen in FIG. 1A. Consequently, the presence of a deletion is clearly indicated in lane 7 of FIG. 1B, whereas lane 7 of FIG. 1A is more difficult to interpret.

Additional aspects of the invention are described in the following sections and illustrated by the Examples.

Choosing the Target Region and the Oligonucleotide Primer

Preferably, a locus associated with a disease such as cancer is chosen. Most preferably, a locus that is known to frequently exhibit one or more deletions is chosen. Useful loci include those containing at most 3 out of the 4 possible nucleotide bases. Preferably, a chosen locus comprises a polynucleotide region in which the deletion is suspected to occur. Once a locus is chosen, primers are designed or chosen to maximize specificity of binding to a nucleotide sequence immediately upstream of the region suspected of containing a deletion. The primer must hybridize immediately upstream of the region suspected of containing the deletion so that no labeled nucleotide is incorporated into the primer extension product.

Sample Preparation and Hybridization

Methods of the invention are performed on any tissue or body fluid, including biopsy samples, and others having a high concentration of affected (i.e., mutated) cells or cellular debris. However, methods of the invention are particularly useful for detecting mutations in heterogeneous biological samples. A preferred sample is stool. For the analysis of stool samples, preferred methods of the invention comprise obtaining at least a cross-section or circumferential portion of a voided stool as taught in U.S. Pat. No. 5,741,650, and co-pending, co-owned U.S. patent application Ser. No. 09/059,718, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA), as taught in co-pending, co-owned U.S. patent application Ser. No. 60/122,177, incorporated by reference herein. It has been discovered that the use of at least 16 mM EDTA, and preferably 100 mM EDTA greatly improves the yield of nucleic acid from stool. Thus, a preferred buffer for stool homogenization comprises phosphate buffered saline, 20–100 mM NaCl or KCl, at least 16 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed.

Nucleic acids to be analyzed are chosen based upon known or suspected relationships between specific mutations and cancer or precancer. If desired, sequence-specific hybrid capture is used to isolate specific nucleic acids from the sample. Target nucleic acids may be analyzed by any method of the art. Examples of preferred methods include enumerative analysis of the loss of heterozygosity as taught in U.S. Pat. No. 5,670,325, incorporated by reference herein. Enumerative methods do not require knowledge of the sequence of a mutant nucleic acid. Rather such methods determine that there has been an alteration (deletion, substitution, addition, rearrangement, or other mutation) in a wild-type nucleic acid. The investigated loci are chosen based upon the likelihood of an alteration being associated with cancer or precancer. Enumerative methods compare the number in a sample of a wild-type nucleic acid known not to be altered in cancer or precancer with the number of a wild-type nucleic acid known or suspected to be altered in cancer or precancer. A statistically-significant difference in the two numbers indicates a positive screen.

Primer Extension, Labeling and Termination

A hybridized primer is extended through the target region using known methods for primer extension, including extension using DNA polymerases. An extended primer preferably is labeled using a detectable label. Preferably, a labeled nucleotide is added to the extended primer once extension through the target region is complete. In a preferred embodiment, the labeled extension reaction is terminated at a predetermined position downstream from the target region. In a preferred embodiment, the labeling and termination steps are performed simultaneously. In one embodiment a labeled terminator nucleotide is incorporated into the extended primer downstream from the target region. Alternatively, the labeling and termination steps are performed separately. Preferably, the labeling and termination reactions are performed at about the same predetermined site downstream from the target region. If not, premature termination of a labeled extension product can interfere with the analysis of the results. Indeed, if a labeled primer extension product must be extended significantly in order to reach the predetermined termination site, then premature termination of the labeled extension product results in a shorter than expected labeled extension product. This short extension product may result in either a false positive indication of a deletion, or creates a background that interferes with the detection of a short extension product resulting from a deletion in the target region. Preferably the labeled base is also a terminator base. More preferably the labeled based is incorporated immediately upstream of the terminator base. Label is preferably a radioactive isotope. Alternatively a fluorescent tag, a molecular weight tag or other detectable label.

Detection and Analysis of the Extension Product

While unlabeled primer extension products are contemplated, in preferred methods of the invention, only extension products that have been extended through the region suspected of containing a deletion are analyzed, because they are the only extension products that contain a detectable label. Extension products that terminate prematurely within the region suspected of containing a mutation are not labeled and are not detected in the assay. Therefore, these premature extension products do not contribute to background noise that interferes with the analysis of the results.

Extended primer products are preferably detected using gel electrophoresis, mass spectroscopy, sequencing, and other methods for determining the differential length of two primers.

The following examples illustrate practice of the invention using deletion detection in the BAT26 and APC 1309 loci on samples prepared from stool specimens.

EXAMPLE 1

Deletion Detection at the BAT26 Locus

Experiments were conducted to demonstrate the usefulness of the invention to detect deletions in the BAT26 locus. The following experiment compares the specificity for detecting deletions at the BAT26 locus using primer extension reactions that incorporate label before extension through the target region versus primer extension reactions that incorporate label at the 3' end of the extension product.

The nucleic acid template was prepared as follows. Template nucleic acid containing the BAT26 locus was amplified by PCR. To each 50 ul PCR reaction tube, 40 ul of washed streptavidin coated Dynal beads were added and mixed by vortexing on a high setting for a few seconds. The mixture was incubated in a rack at room temperature for 15 minutes, and mixed by vortexing after 5 minutes and 10 minutes of the incubation period. The tube was placed in a magnetic tube holder, and the supernatant was removed. A 100 ul aliquot of 2X Binding & Wash buffer was added to each sample, and vortexed on a high setting for a few seconds. The tube was again placed in a magnetic tube holder and the supernatant was removed. A 100 ul aliquot of 0.1 M NaOH was added to each tube, and mixed by vortexing on high for a few seconds. After a 5 minute incubation at room temperature, the tubes were placed in a magnetic tube holder, and the supernatant was removed. A further 100 ul of 0.1 M NaOH was added, and vortexed for a few seconds. After placing the tube in a magnetic tube holder and removing the supernatant, 100 ul of 1X Binding & Washing buffer was added and vortexed for a few seconds on a high setting. The tube was placed in a magnetic tube holder, the supernatant was removed, and 100 ul of 1X TE pH 8.0 was added. The tube was vortexed on high for a few seconds, placed in a magnetic tube holder, and the supernatant was removed. The beads were resuspended in 100 ul of 0.1X TE pH 8.0 buffer by vortexing on high for a few seconds. The resulting samples were used in the assays, and may be stored at 4C for up to 1 month.

In a first experiment, 5 ul of bead-bound PCR product was added to the following primer extension reaction mixture: 9.625 ul of sterile molecular biology grade diH20, 2.5 ul of 10X Sequenase Buffer, 2.5 ul of 5 uM primer 1, 2.5 ul of 2 mM dATP, 2.5 ul of 50 uM ddGTP, 0.125 ul of 32P dTTP, and 0.25 ul of Sequenase.

The reaction mixture was cycled in an MJ Research Tetrad Thermalcycler according to the following temperature profile.

| Temperature | Time | # Cycles |
| --- | --- | --- |
| 94 C. | 5 min | 1 |
| 94 C. | 30 sec | |
| 52 C. | 10 sec | 30 |
| 72 C. | 10 sec | |
| 4 C. May be taken out of cycler immediately or after overnight run | | |

A 15 ul aliquot of formamide based stop solution was added to each sample and mixed by pipetting up and down 5 times. A 7 ul aliquot from each sample was analyzed using a 15% denaturing polyacrylamide gel with 7M Urea in 1X TBE running buffer. The gel was dried and analyzed using a Packard Instant Imager. Results are shown in FIG. 1A. Lanes 1–8 are analyses of DNA obtained from patient stool samples. Lanes 9–14 are controls. Lane 9 contains no DNA template. Lanes 10, 13, and 14 contain, respectively, 0%, 1%, and 5% mutant DNA with a deletion within the polyA stretch of the BAT26 locus. Lanes 11 and 12 are no PCR controls.

In a second experiment, 5 ul of bead bound PCR product was added to the following primer extension reaction mixture: 7.125 ul of sterile molecular biology grade diH 20, 2.5 ul of 10X Sequenase Buffer, 2.5 ul of 5 uM primer 2, 2.5 ul of 2 mM dATP, 2.5 ul of 50 uM ddTTP, 2.5 ul of 0.1 uM dGTP, 0.125 ul of 32P dGTP, and 0.25 ul of Sequenase.

The reaction mixture was exposed to the same temperature cycling as the reaction mixture in the first experiment, and the products were separated on a polyacrylamide gel under the same conditions. Lanes 1–14 of FIG. 1B show results of this second experiment. The same nucleic acid templates were used in the reactions shown in lanes 1–14 of FIG. 1A and lanes 1–14 of FIG. 1B.

In the first experiment, shown in FIG. 1A, the radioactive dGTP was incorporated into the primer extension product before it was extended through the polyA stretch of the BAT26 locus. Primer 1 (5'-AGCCCTTAACCTTTTTCAGG-3', SEQ ID No: 1) used in the first experiment, hybridizes immediately upstream of a site where dTTP is incorporated (an A on the template strand). Accordingly, prematurely terminated extension products are labeled and appear as background in all of lanes 1–8.

In the second experiment, shown in FIG. 1B, the radioactive dTTP was incorporated into the primer extension product after it was extended through the polyA stretch of the BAT26 locus. The 3' end of primer 2 (5'-GCCCTTAACCTTTTTCAGGT3', SEQ ID NO: 2) used in the second experiment, includes the T that is immediately downstream from primer 1. Accordingly, in the second reaction, radioactive dTTP is only incorporated into the primer extension product after it has been extended through the polyA stretch. Furthermore, the extension reaction is also terminated close to the site of 32P dGTP incorporation. The second reaction mixture also contains ddTTP, and some of the extension products incorporate 32PdGTP followed by ddTTP at the T repeat downstream from the polyA stretch. Accordingly, in the second experiment, primer extension products that terminate prematurely within the polyA stretch are not labeled and are not seen as background in lanes 1–8, nor in control lanes 9–14. In FIG. 1B, only lanes 6 and 7, and control lanes 13 and 14, contain short labeled primer extension product. The only samples that contained nucleic acid template having a deletion in the polyA stretch were the ones that were analysed in lanes 6, 7, 13, and 14. The sample of lane 6 was contaminated with a small amount of deleted template. The sample of lane 7 was from a patient with colon cancer associated with a deletion in the polyA stretch of the BAT26 locus. The samples of lanes 13 and 14 contained 1% and 5% mutant DNA, respectively.

A comparison of FIGS. 1A and 1B, shows that methods of the invention reduce the background of primer extension reactions. As a result, the analysis is much easier to interpret. Indeed, the presence of smaller than expected extension products in the second experiment is an indicator of the presence of mutant nucleic acid in the sample. In the first experiment, smaller than expected extension products are present in all reactions, and the analysis is more complicated.

In addition, methods of the invention, illustrated by the results of the second experiment, can be used to detect a very small amount of mutant nucleic acid in a heterogeneous sample containing mainly normal nucleic acid. The results shown in lanes 6 and 13 are the most striking. In FIG. 1A, it is difficult to decide whether a deletion product is present in lanes 6 and 13. In contrast, a deletion product is clearly present in lanes 6 and 13 of FIG. 1B.

Methods of the invention are particularly useful for analyzing loci such as BAT26, where a stretch of repeated nucleotide sequence interferes the with efficient extension of DNA polymerase reactions. Premature termination of extension reactions is typically more frequent at such loci.

EXAMPLE 2

Deletion Detection at the APC 1309 Locus

A deletion of 5 nucleotides is often found at codon 1309 of the APC gene. The nucleotide sequence at this location is 5'-GAAAAGATT-3'(SEQ ID NO: 3) in the wild-type gene. Typical deletions consist of GAAAA (SEQ ID NO: 4), AAAAG (SEQ ID NO: 5), or AAAGA (SEQ ID NO: 6). To detect any of these deletions using a method of the invention, a 17 base oligonucleotide was designed to hybridize immediately upstream of the position of the first G (the G of the GAA codon above). Hybridized primer was extended in the presence of unlabeled dATP, unlabeled dGTP, and 33P-ddTTP. Accordingly, the extension product is only labeled if it is extended through the target region suspected of containing a deletion and the labeled ddTTP is incorporated. The expected wild-type product is 25 bases long, whereas any of the deletions described above generates a 20 base long extension product.

Figure 2:
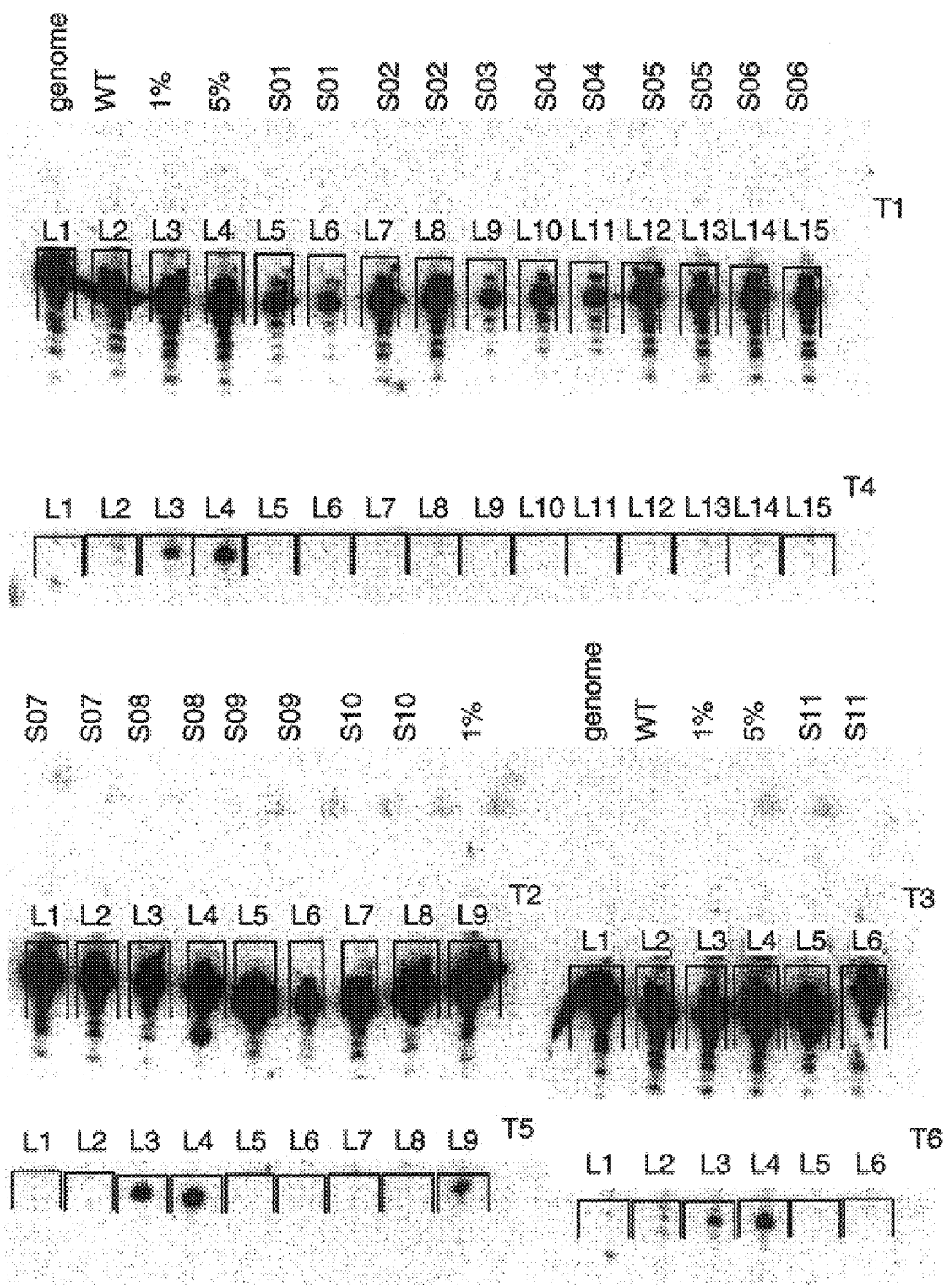
FIG. 2 shows deletion detection at the APC1309 locus.

The extension reaction was performed on a duplicates of patient samples and the results are shown in FIG. 2. Controls containing 0%, 1%, and 5% mutant nucleic acid were also analyzed that contained a 5 bp deletion in BAT26. The control results indicate that the presence of 1% mutant nucleic can be detected unambiguously. Both tests for patient #508 indicated the presence of a deletion at the 1309 locus. Patient 508 did indeed have colon cancer associated with a deletion at the 1309 locus.

In contrast, the results for patients without a deletion at the 1309 locus showed no background at the position characteristic of a deletion containing extension product. Accordingly, methods of the invention are useful for a simple test for the presence of a deletion at the 1309 locus.

What is claimed is:

1. A method for detecting a nucleic acid insertion or deletion, the method comprising the steps of:
   a) selecting a nucleic acid having a known wild-type sequence and having a target region comprising at most three different types of nucleotide bases selected from the group consisting of dGTP, dATP, dTTP, and dCTP;
   b) contacting a sample with an oligonucleotide primer that is complementary to a portion of said nucleic acid immediately upstream of said target region;
   c) extending said primer in the presence of nucleotide bases that are complementary to the nucleotide bases of the target region, thereby to form a primer extension product;
   d) extending the primer extension product in the presence of a labeled nucleotide complementary to a nucleotide base downstream from the target region in said nucleic acid, wherein said labeled nucleotide is not complementary to any of the nucleotide bases of the target region selected in step (a); and,
   e) comparing the size of the labeled extension product obtained in step d) to a standard, wherein a labeled extension product smaller than the standard is indicative of the presence of a deletion in the target region and a labeled extension product larger than the standard is indicative of the presence of an insertion in the target region.

2. The method of claim 1, further comprising the step of terminating the primer extension product by incorporating a terminator nucleotide in said product that is complementary to a nucleotide downstream from the target region in a wild type nucleic acid, wherein said terminator nucleotide is not complementary to any of the nucleotides of the target region selected in step (a), said step of terminating the primer extension product being performed simultaneously with or immediately after step (d).

3. The method of claim 2, wherein the labeled nucleotide and the terminator nucleotide are the same.

4. The method of claim 2, wherein more than one labeled nucleotide is incorporated into the extension product prior to incorporation of the terminator nucleotide.

5. The method of claim 1, wherein the labeling reaction of step (d) is performed in the presence of labeled nucleotide and unlabeled nucleotide of the same type.

6. The method of claim 5, wherein the ratio of labeled nucleotide base to unlabeled nucleotide base is 1:1.6 (unlabeled:labeled).

7. The method of claim 5, wherein more than one nucleotide from step (d) is incorporated into the labeled extension product.

8. The method of claim 7, wherein only one of the incorporated nucleotides is labeled.

9. The method of claim 1, wherein said sample contains a heterogeneous mixture of mutant nucleic acid having a deletion in the target region and wild type nucleic acid with no deletion in the target region.

10. The method of claim 9, wherein a deletion in the target region is present in from about 1% to about 5% of the nucleic acid molecules containing the target region.

11. The method of claim 1, wherein said sample is selected from the group consisting of stool, homogenized stool, urine, semen, blood, saliva, sputum, cerebrospinal fluid, pancreatic juice, pus, and aspirate.

12. The method of claim 1, wherein said samples is a biological sample, and wherein a deletion in the target region is indicative of the presence of cancerous or precancerous tissue in the biological sample.

13. The method of claim 12, wherein said cancerous or precancerous tissue is of colorectal origin.

14. The method of claim 1, wherein said sample includes a buffer comprising at least 100 mM EDTA.

15. The method of claim 1, wherein said target region is a BAT- 26 nucleic acid region.

16. The method of claim 1, wherein said target region is selected from the group consisting of APC, DCC, p53 and RAS nucleic acid regions.

17. The method of claim 1, wherein said target region is a microsatellite region.

18. The method of claim 1, wherein the presence of a deletion in said target region is associated with the presence of a mutation at a separate genetic locus selected from the group consisting of BAT26, APC, DCC, P53, and RAS genetic loci.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Primer 1

<400> SEQUENCE: 1
agcccttaac cttttttcagg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Primer 2

<400> SEQUENCE: 2
gcccttaacc tttttcaggt                                               20

<210> SEQ ID NO 3
<211> LENGTH: 9
<212> TYPE: DNA
<213> ORGANISM: Homo sapiens
<220> FEATURE:
<223> OTHER INFORMATION: wild-type APC sequence at codon 1309
```

```
<400> SEQUENCE: 3 gaaaagatt                                                                        9

<210> SEQ ID NO 4
<211> LENGTH: 5
<212> TYPE: DNA
<213> ORGANISM: Homo sapiens
<220> FEATURE:
<223> OTHER INFORMATION: typical deletion at APC codon 1309

<400> SEQUENCE: 4 gaaaa                                                                            5

<210> SEQ ID NO 5
<211> LENGTH: 5
<212> TYPE: DNA
<213> ORGANISM: Homo sapiens
<220> FEATURE:
<223> OTHER INFORMATION: typical deletion found at APC codon 1309

<400> SEQUENCE: 5 aaaag                                                                            5

<210> SEQ ID NO 6
<211> LENGTH: 5
<212> TYPE: DNA
<213> ORGANISM: Homo sapiens
<220> FEATURE:
<223> OTHER INFORMATION: typical deletion found at APC codon 1309

<400> SEQUENCE: 6 aaaga                                                                            5
```